United States Patent
Nithiyanandam et al.

(10) Patent No.: US 10,918,604 B2
(45) Date of Patent: Feb. 16, 2021

(54) SOLID ORAL DOSAGE FORMS OF ESLICARBAZEPINE

(71) Applicant: Jubilant Generics Limited, Uttar Pradesh (IN)

(72) Inventors: Ravikumar Nithiyanandam, Coimbatore (IN); Ganesh Vinayak Gat, Pune (IN); Dinesh Kumar, Chandigarh (IN); Kamal S. Mehta, Noida (IN); Premchand Dalichandji Nakhat, Yavatmal (IN); Vivek Jain, Ghaziabad (IN); Priyank Sharma, Alwar (IN); Baibhav Joshi, Noida (IN)

(73) Assignee: Jubilant Generics Limited

( * ) Notice: Subject to any disclaimer, the term of this patent is extended or adjusted under 35 U.S.C. 154(b) by 134 days.

(21) Appl. No.: 15/742,004

(22) PCT Filed: Dec. 16, 2016

(86) PCT No.: PCT/IB2016/057716
§ 371 (c)(1),
(2) Date: Jan. 4, 2018

(87) PCT Pub. No.: WO2017/103876
PCT Pub. Date: Jun. 22, 2017

(65) Prior Publication Data
US 2018/0280307 A1    Oct. 4, 2018

(30) Foreign Application Priority Data
Dec. 18, 2015  (IN) .......................... 4163/DEL/2015

(51) Int. Cl.
*A61K 9/20*   (2006.01)
*A61K 31/55*  (2006.01)
*A61K 9/00*   (2006.01)

(52) U.S. Cl.
CPC .......... *A61K 9/2054* (2013.01); *A61K 9/0053* (2013.01); *A61K 9/2013* (2013.01); *A61K 9/2018* (2013.01); *A61K 9/2027* (2013.01); *A61K 9/2059* (2013.01); *A61K 9/2077* (2013.01); *A61K 31/55* (2013.01); *A61K 9/205* (2013.01)

(58) Field of Classification Search
CPC .. A61K 9/2054; A61K 9/2018; A61K 9/2059; A61K 9/2077; A61K 9/0053; A61K 31/55; A61K 9/20; A61K 9/2004; A61K 9/2013; A61K 9/2022; A61K 9/2027
See application file for complete search history.

(56) References Cited

U.S. PATENT DOCUMENTS 8,372,431 B2 * 2/2013 Cardoso de Vasconcelos ............. A61K 9/0056
424/465
2014/0302152 A1 * 10/2014 Da Costa Barrocas ..................... A61K 9/1623
424/490

OTHER PUBLICATIONS

H.V. Kamp, G.K. Bolhuis, C.F. Lerk. Improvement by super disintegrants of the properties of tablets containing lactose, prepared by wet granulation I. Pharmaceutisch Weekblad Sci. Ed., 5 (1983), pp. 165-171 (Year: 1983).*
West, Anthony R., Solid State Chemistry and its Applications, Wiley, New York, 1988, pp. 358 & 365 (Year: 1988).*

* cited by examiner

*Primary Examiner* — Lakshmi S Channavajjala
(74) *Attorney, Agent, or Firm* — Sarika Singh, Esq.; McNeely, Hare & War, LLP

(57) ABSTRACT

The present invention relates to high drug load pharmaceutical compositions comprising Eslicarbazepine or its pharmaceutically acceptable salts, esters, solvates, polymorphs, enantiomers or mixtures thereof. The present invention also relates to a process for preparing high drug load solid oral pharmaceutical composition comprising Eslicarbazepine acetate and at least one pharmaceutically acceptable excipient. The prior art highlights various technical challenges for formulation development of Eslicarbazepine acetate at lab as well as at industrial scale and offer restrictive and complex approach for resolution of technical challenges. Compositions of Eslicarbazepine acetate prepared as per present invention, wherein disintegrant and/or binder is present in either intra-granular part or in extra-granular part of the composition exhibited desirable technical attributes like comparable dissolution and bioequivalence against reference listed drug.

16 Claims, No Drawings

SOLID ORAL DOSAGE FORMS OF ESLICARBAZEPINE

FIELD OF THE INVENTION

The present invention relates to high drug load pharmaceutical composition of an anticonvulsant drug or its pharmaceutically acceptable salts, esters, solvates, polymorphs, enantiomers or mixtures thereof. In particular, but without restriction to the particular embodiments hereinafter described in accordance with the best mode of practice, present invention provides a high drug load solid oral pharmaceutical composition comprising Eslicarbazepine or its pharmaceutically acceptable salts, esters, solvates, polymorphs, enantiomers or mixtures thereof and process for preparing the same.

BACKGROUND OF THE INVENTION

Eslicarbazepine acetate is a voltage-gated sodium channel blocker, providing anticonvulsant effect and used in the treatment of partial-onset seizures as monotherapy or adjunctive therapy. Eslicarbazepine acetate is chemically known as (S)-10-acetoxy-10,11-dihydro-5H-dibenzo[b,f]azepine-5-carboxamide and is represented by the following formula:

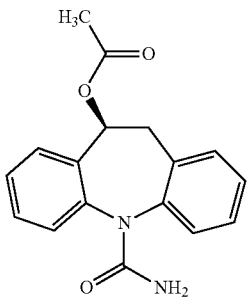 [SMILES: CC(=O)O[C@H]1Cc2ccccc2N(C(N)=O)c2ccccc21]

Eslicarbazepine acetate is commercially marketed as APTIOM® by Sunovion Pharmaceuticals as an immediate release tablet in strengths of 200, 400, 600, and 800 mg. APTIOM® tablets contain Eslicarbazepine acetate along with inactive ingredients as povidone, croscarmellose sodium and magnesium stearate. Following patent publications pertain to various formulations of Eslicarbazepine acetate:

U.S. Pat. No. 5,753,646 assigned to Bial-Portela describes dihydrodibenzo [b,f] azepines derivatives including Eslicarbazepine acetate and a process for the preparation of Eslicarbazepine acetate. This patent publication also teaches use of dihydrodibenzo [b,f] azepines derivatives in the treatment of central and peripheral nervous system disorders including epilepsy, trigeminal neuralgia, affective brain disorders and nervous function changes in degenerative and post-ischemic diseases.

Eslicarbazepine acetate is reported to be poorly soluble in water which leads to poor dissolution and administration of a high dose of the drug in order to attain desired therapeutic effect. Poor aqueous solubility, flowability, compressibility and high dose of the drug also pose technical challenges to formulation scientist in development of a suitable formulation with desired technical attributes.

US Patent publication No. 2007/0196488 assigned to Novartis AG discloses oral controlled release compositions of Eslicarbazepine with lipophilic or hydrophilic swellable substance. This patent publication suggests use of median particle size in range of about 20 to about 50 μm for the preparation of controlled release compositions of Eslicarbazepine.

US Patent publication No. US 2014/0302152 assigned to Bial-Portela discloses granular pharmaceutical dosage form of Eslicarbazepine acetate with one or more pharmaceutically acceptable excipients.

U.S. Pat. No. 8,372,431 and US Patent publication No. 2014/0343043 assigned to Bial-Portela discloses pharmaceutical composition of Eslicarbazepine acetate prepared by granulation process wherein disintegrant is essentially present in both intra-granular as well as extra-granular portion of the composition in equal proportion. The said publication teaches use of povidone as binder and croscarmellose sodium as preferred disintegrant in a specific amount 3%-10% w/w on basis of total weight of the composition. The patent publication highlights various technical challenges for formulation development of Eslicarbazepine acetate at lab as well as at industrial scale and offer restrictive and complex approach for resolution of technical challenges.

The pharmaceutical compositions of Eslicarbazepine acetate suitable for oral administration to humans must have desirable chemical and physical properties, dissolution, stability and bioequivalence complying with demanding requirements and regulations of health and medicine regulatory agencies across the world, especially USFDA, MHRA and TGA.

The prior art discloses complex approaches for formulating Eslicarbazepine acetate into suitable dosage form like use of a) specific excipients povidone as binder, croscarmellose sodium as disintegrant b) half of disintegrant in intra-granular part and half of disintegrant in extra-granular part, c) half of binder in intra-granular part in powder form and half of binder in granulation liquid. Thus, there is a need of alternate dosage form of Eslicarbazepine acetate with desirable technical formulation attributes such as dissolution, stability, bioequivalence and manufactured by simple, reproducible and commercially viable process at lab as well as at industrial scale.

The present inventors have developed an alternate dosage form of Eslicarbazepine acetate and unexpectedly found that the addition of a disintegrant and/or a binder in intra-granular or in extra-granular part of the composition offers desirable formulation characteristics like dissolution, stability and bioequivalence that is comparable to the commercially available counterpart (APTIOM® Tablets). Further, the process employed in the manufacture of dosage form of Eslicarbazepine acetate is consistent and therefore feasible for industrial production.

OBJECTS AND SUMMARY OF THE INVENTION

It is a principal object of the present invention to provide a high drug load pharmaceutical composition comprising Eslicarbazepine or its pharmaceutically acceptable salts, esters, solvates, polymorphs, enantiomers or mixtures thereof with one or more pharmaceutically acceptable excipient.

It is another object of the present invention to provide a process for the preparation of high drug load pharmaceutical composition comprising Eslicarbazepine or its pharmaceutically acceptable salts, esters, solvates, polymorphs, enantiomers or mixtures thereof.

It is another object of the present invention to provide a high drug load pharmaceutical composition comprising Eslicarbazepine or its pharmaceutically acceptable salt present in an amount of more than 60% by weight based on the total weight of the composition. In particular, the amount of Eslicarbazepine or its pharmaceutically acceptable salt may vary from about 60% to about 97% by weight, based on the total weight of the composition.

It is another object of the present invention to provide a high drug load solid oral pharmaceutical composition comprising Eslicarbazepine or its pharmaceutically acceptable salts, esters, solvates, polymorphs, enantiomers or mixtures thereof, further comprising at least one or more pharmaceutically acceptable excipients like diluent, binder, disintegrant, glidant, surfactant, wetting agent, lubricant, solubilizer, stabilizer, sweetener, flavoring agent and coloring agent.

Another object of the present invention is to develop high drug load pharmaceutical compositions of Eslicarbazepine acetate that make the granulation process more consistent and therefore feasible for industrial production, while maintaining stability and pharmaceutical equivalence to the reference listed drug.

The following embodiments further describe the objects of the present invention in accordance with the best mode of practice, however, disclosed invention is not restricted to the particular embodiments hereinafter described.

In accordance with a preferred embodiment of the present invention, there is provided a high drug load pharmaceutical composition comprising granules of Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein disintegrant is present either in intra-granular or in extra-granular part of composition.

In accordance with another embodiment of the present invention, there is provided a high drug load pharmaceutical composition comprising granules of Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein extra-granular part of the composition is free of disintegrant.

In accordance with yet another embodiment of the present invention, there is provided a high drug load pharmaceutical composition comprising Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein the composition comprises disintegrant in an amount from about 0% to about 12% w/w by total weight of the composition.

In accordance with one other embodiment of the present invention, there is provided a high drug load pharmaceutical composition comprising Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein the composition comprises disintegrant in an amount of less than 3% w/w or more than 10% w/w by total weight of the composition.

In accordance with yet another embodiment of the present invention, there is provided a high drug load pharmaceutical composition comprising granules of Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein binder is present either in intra-granular or in extra-granular part of composition.

In accordance with yet another embodiment of the present invention, there is provided a high drug load pharmaceutical composition comprising granules of Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein binder is present in intra-granular part of the composition in dispersion form (granulation liquid/binder solution) and intra-granular part of the composition is free of any dry binder.

In accordance with still another embodiment of the present invention, there is provided a high drug load pharmaceutical composition comprising granules of Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein a) intra-granular part of the composition comprises disintegrant and optionally binder in dry powder form and/or dispersion form and b) extra-granular part of the composition is free of disintegrant and/or binder.

In accordance with still another embodiment of the present invention, there is provided a high drug load pharmaceutical composition comprising Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein the composition comprises binder in an amount of less than 3% w/w or more than 10% w/w by total weight of the composition.

In accordance with still another embodiment of the present invention, there is provided a high drug load pharmaceutical composition comprising Eslicarbazepine or its pharmaceutically acceptable salts, esters, solvates, polymorphs, enantiomers or mixtures thereof and at least one or more pharmaceutically acceptable excipient including a binder, a disintegrant and a lubricant, wherein the composition further comprise optionally a diluent and/or a wetting agent.

In accordance with still another embodiment of the present invention, there is provided a high drug load pharmaceutical composition comprising Eslicarbazepine or its pharmaceutically acceptable salts, esters, solvates, polymorphs, enantiomers or mixtures thereof prepared by wet granulation, dry granulation, dry blending, dry mixing or direct compression process.

In accordance with still another embodiment of the present invention, there is provided a process for the preparation of a high drug load pharmaceutical composition comprising Eslicarbazepine or its pharmaceutically acceptable salts, esters, solvates, polymorphs, enantiomers or mixtures thereof comprising the steps of a) Sifting the accurately weighed quantities of active agent and one or more pharmaceutically acceptable excipient(s) through a suitable sieve followed by mixing; b) Granulating the mixture of step a) with an binder solution (granulation in an aqueous or non-aqueous solvent); c) Drying the granulated mass, optionally milling of the dried granules and mixed the sifted granules; d) lubricated the sifted blend of step c); e) Compressing the lubricated granules into tablets or filling in capsules.

In accordance with still another embodiment of the present invention, there is provided a high drug load pharmaceutical composition comprising Eslicarbazepine or its pharmaceutically acceptable salts, esters, solvates, polymorphs, enantiomers or mixtures thereof comprising the steps of: (a) blending a mixture of Eslicarbazepine acetate and at least one pharmaceutically acceptable excipient including a binder and/or a disintegrant; (b) optionally compacting the blended material using roller compactor; (c) optionally milling the compacted material; (d) blend from step (a) or milled material from step (c) was lubricated with a suitable lubricant; (e) lubricated blend or granules from (d) was compressed into tablets with a suitable tooling or filled in capsules.

In accordance with still another embodiment of the present invention, there is provided a high drug load solid oral dosage form comprising a pharmacologically effective amount of Eslicarbazepine or its pharmaceutically acceptable salts, esters, solvates, polymorphs, enantiomers or mixtures thereof, wherein the granules used in the composition exhibit desirable flowability and compressibility to reference listed drug.

In accordance with still another embodiment of the present invention, there is provided a high drug load solid oral dosage form comprising a pharmacologically effective amount of Eslicarbazepine or its pharmaceutically acceptable salts, esters, solvates, polymorphs, enantiomers or mixtures thereof present in an amount of about 30% to about 95% by weight wherein, the composition exhibits technical attributes such as tablet size, dissolution, stability and bioequivalence that is comparable to the commercially available counterpart (APTIOM® Tablets) and a process for preparing the same.

In accordance with still another embodiment of the present invention, there is provided a high drug load pharmaceutical composition comprising Eslicarbazepine or its pharmaceutically acceptable salts, esters, solvates, polymorphs, enantiomers or mixtures thereof, wherein Eslicarbazepine acetate has a particle size distribution $D_{90}$ less than about 200 µm, $D_{50}$ less than about 100 µm and $D_{10}$ less than about 50 µm.

In accordance with still another embodiment of the present invention, there is provided a high drug load pharmaceutical composition which is stable at 40° C. and 75% relative humidity.

In accordance with still another embodiment of the present invention, there is provided a high drug load solid pharmaceutical compositions comprising Eslicarbazepine acetate or its pharmaceutically acceptable salts, esters, solvates, polymorphs, enantiomers or mixtures thereof, wherein the composition is substantially free from other polymorphic forms.

In accordance with still another embodiment of the present invention, there is provided use of high drug load pharmaceutical composition of the present invention in the manufacture of a medicament for treating epilepsy, partial-onset seizures as a monotherapy or adjunctive therapy, affective disorders, neuropathic pain, motor impairment, fibromyalgia, post-herpetic neuralgia, bipolar disorder, schizoaffective disorders, attention disorders, and anxiety disorders.

DESCRIPTION OF THE INVENTION

The present invention can be more readily understood by reading the following detailed description of the invention and study of the included examples.

As used herein, the term "composition", as in pharmaceutical composition, is intended to encompass a drug product comprising an anticonvulsant drug, preferably Eslicarbazepine or its pharmaceutically acceptable salts, esters, solvates, polymorphs, enantiomers or mixtures thereof, and other inert ingredient(s) (pharmaceutically acceptable excipients). Such pharmaceutical compositions are synonymous with "formulation" and "dosage form". Pharmaceutical composition of the invention include, but is not limited to, granules, tablets (single layered tablets, multilayered tablets, bioadhesive tablets, caplets, matrix tablets, tablet within a tablet, mucoadhesive tablets, modified release tablets, pulsatile release tablets, timed release tablets, delayed release, controlled release, extended release and sustained release tablets), capsules (immediate or modified release) (hard and soft or liquid filled soft gelatin capsules), pills, troches, sachets, powders, microcapsules, mini-tablets, tablets in capsules and microspheres, matrix composition and the like. Preferably, the pharmaceutical composition refers to tablets and capsules. More preferably, the pharmaceutical composition refers to immediate release oral tablets, which may be uncoated or film coated.

As used herein, the term "Eslicarbazepine" is used in broad sense to include not only "Eslicarbazepine" per se but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable isomers, pharmaceutically acceptable polymorphs, pharmaceutically acceptable prodrugs thereof, and also its various crystalline and amorphous forms. The term "Eslicarbazepine acetate" used in this specification means the S-isomer in substantially pure form, i.e. at least about 98% pure.

The term "high drug load" as used herein, refers from about 30% to about 97% by weight of Eslicarbazepine acetate based on the total weight of the composition.

The term "excipient" means a pharmacologically inactive component such as a diluent, binder, disintegrant, glidant, surfactant, wetting agent, lubricant, solubilizer, stabilizer sweetener, flavoring agent, coloring agent and the like. The excipients that are useful in preparing a pharmaceutical composition are generally safe, non-toxic and are acceptable for veterinary as well as human pharmaceutical use. Reference to an excipient includes both one and more than one such excipient. Co-processed excipients are also covered under the scope of present invention. The excipient(s) may be present intra-granularly or extra-granularly or in both the phases in any form. Further, excipient may be in the form of powders or in the form of dispersion. Combination of excipients performing the same function may also be used to achieve desired formulation characteristics.

"Substantially free" as used herein refers to the pharmaceutical composition of Eslicarbazepine acetate, which is free from conversion to other polymorphic forms during formulation development or stability studies.

As used in this specification, the singular forms "a", "an", and "the" include plural references unless the context clearly dictates otherwise. Thus, for example, a reference to "a process" includes one or more process, and/or steps of the type described herein and/or which will become apparent to those persons skilled in the art upon reading this disclosure and so forth.

As used herein, the term "intra-granular" (part/phase/portion) refers to the components of formulation of the present invention that are within granules. As used herein, the term "extra-granular" (part/phase/portion) refers to those components of formulation of the present invention that are outside the granules.

Unless otherwise stated the weight percentages expressed herein are based on the final weight of the composition or formulation.

The pharmaceutical compositions of present invention comprise about 1 to about 1600 mg of Eslicarbazepine acetate, preferably about 200 to about 800 mg of Eslicarbazepine acetate. The pharmaceutical composition comprises Eslicarbazepine acetate in the range of about 30% to about 97% by weight, preferably in the range of about 60% to about 95% by weight on the basis of the total weight of the composition.

In another embodiment the high drug load pharmaceutical composition of the present invention includes particle size of Eslicarbazepine acetate or its pharmaceutically acceptable salts, esters, solvates, polymorphs, enantiomers or mixtures thereof, having a particle size distribution such that $D_{90}$ is less than about 200 µm, $D_{50}$ is less than about 100 µm and $D_{10}$ is less than about 50 µm. The particle size of Eslicarbazepine acetate can be measured by suitable techniques such as Laser light scattering (e.g. Malvern Light Scattering), Coulter counter, microscopy and any other technique known in the art.

In another embodiment, the present invention includes a high drug load solid oral pharmaceutical composition comprising from about 30% to about 95% by weight of Eslicarbazepine acetate based on the total weight of the composition wherein, the composition is substantially free of other polymorphic forms.

In another embodiment of the invention, the high drug load solid oral pharmaceutical composition comprising Eslicarbazepine acetate is prepared by wet or dry process. The wet and dry processes include, but are not limited to, wet granulation, dry granulation, dry blending, dry mixing and direct compression. Other formulation techniques are also contemplated within the scope of the present invention. Any pharmaceutically acceptable granulating agent can be used for wet granulation. Preferable granulating solvents include, but are not limited to, water, esters such as ethyl acetate; ketones such as acetone; alcohols such as methanol, ethanol, isopropanol, butanol; dichloromethane, chloroform, dimethyl acetamide (DMA), dimethyl sulfoxide (DMSO), ether, diethyl ether and combinations thereof. Preferably, the granulating solvent used during wet granulation is water.

In another embodiment of the invention, wet granulation can be performed using Rapid mixer granulator, Fluid bed granulator, Planetary mixer and the like; dry blending can be performed using V-blender or key blender; and dry granulation can be performed using roller compacter or slugging techniques or by any other method known in the art.

In another embodiment of the invention, there is provided a process for the preparation of a high drug load pharmaceutical composition comprising Eslicarbazepine or its pharmaceutically acceptable salts, esters, solvates, polymorphs, enantiomers or mixtures thereof comprising the steps of a) Sifting the accurately weighed quantities of active agent and one or more pharmaceutically acceptable excipient(s) through a suitable sieve followed by mixing; b) Granulating the mixture of step a) with an binder solution (granulation in an aqueous or non-aqueous solvent); c) Drying the granulated mass, optionally milling of the dried granules and mixed the sifted granules; d) lubricated the sifted blend of step c); e) Compressing the lubricated granules into tablets or filling in capsules.

In another embodiment of the invention, there is provided a high drug load pharmaceutical composition comprising Eslicarbazepine or its pharmaceutically acceptable salts, esters, solvates, polymorphs, enantiomers or mixtures thereof comprising the steps of: (a) blending a mixture of Eslicarbazepine acetate and at least one pharmaceutically acceptable excipient including a binder and/or a disintegrant; (b) optionally compacting the blended material using roller compactor (c) optionally milling the compacted material; (d) blend from step (a) or milled material from step (c) was lubricated with a suitable lubricant; (e) lubricated blend or granules from (d) was compressed into tablets with a suitable tooling or filled in capsules.

In another embodiment of the invention, there is provided a process for preparation of high drug load pharmaceutical composition comprising Eslicarbazepine acetate, wherein the process is easily scalable at an industrial scale.

In another embodiment of the present invention there is provided a high drug load solid oral pharmaceutical composition comprising Eslicarbazepine or its pharmaceutically acceptable salts, esters, solvates, polymorphs, enantiomers or mixtures thereof, wherein the composition comprises at least one or more pharmaceutically acceptable excipient like diluent, binder, disintegrant, glidant, surfactant, wetting agent, lubricant, solubilizer, stabilizer, sweetener, flavoring agent and coloring agent.

Embodiments of the present invention also relate to high drug load pharmaceutical compositions of Eslicarbazepine or its pharmaceutically acceptable salts, esters, solvates, polymorphs, enantiomers or mixtures thereof, and at least one or more pharmaceutically acceptable excipient including a binder, a disintegrant and a lubricant, wherein the composition comprises a binder and/or a disintegrant present in an amount from about 0% to 12% w/w by total weight of the composition which is present in intra-granular part of composition.

Embodiments of the present invention relate to high drug load pharmaceutical compositions of Eslicarbazepine or its pharmaceutically acceptable salts, esters, solvates, polymorphs, enantiomers or mixtures thereof, and at least one or more pharmaceutically acceptable excipient including a binder, a disintegrant and a lubricant, wherein the composition comprises a binder and/or a disintegrant less than 3% w/w or more than 10% w/w by total weight of the composition.

Embodiments of the present invention also relate to high drug load pharmaceutical compositions of Eslicarbazepine or its pharmaceutically acceptable salts, esters, solvates, polymorphs, enantiomers or mixtures thereof, and at least one or more pharmaceutically acceptable excipient including a binder, a disintegrant and a lubricant, wherein the composition comprises a binder and/or a disintegrant which is present either in intra-granular or in extra-granular part of composition.

Embodiments of the present invention also relate to high drug load solid oral pharmaceutical compositions of Eslicarbazepine or its pharmaceutically acceptable salts, esters, solvates, polymorphs, enantiomers or mixtures thereof, and at least one or more pharmaceutically acceptable excipient, wherein the composition exhibits more than 80% of drug release within 30 minutes in 1000 ml of Acetate Buffer, pH 4.5 (Office of Generic Drugs dissolution database) using USP II apparatus (Paddle) at a temperature of 37±0.5° C. and a rotation speed of 100 revolutions per minute.

The compositions of the present invention comprise Eslicarbazepine or a pharmaceutically acceptable salts thereof having $D_{90}$ less than or equal to about 200 µm. Preferably, $D_{90}$ is less than or equal to about 100 µm. More preferably, $D_{90}$ is less than or equal to about 30 µm. The particle size of Eslicarbazepine acetate can be measured by techniques such as Laser light scattering (e.g. Malvern Light Scattering), Coulter counter, microscopy and the like.

Various useful fillers or diluents include, but are not limited to microcrystalline cellulose ("MCC"), sodium alginate, silicified MCC (e.g., PROSOLV™), microfine cellulose, lactitol, cellulose acetate, kaolin, lactose, maltose, trehalose, starch, pregelatinized starch, sucrose, mannitol, xylitol, sorbitol, dextrates, dextrin, maltodextrin, compressible sugar, confectioner's sugar, dextrose, polydextrose, simethicone, fructose, calcium carbonate, calcium sulfate, calcium phosphate, dibasic calcium phosphate dihydrate, tribasic calcium phosphate, magnesium carbonate, magnesium oxide and mixtures thereof. Preferably, diluent is microcrystalline cellulose (MCC) or lactose or any combination thereof. Preferably, the amount of diluent is from about 0% to about 80.0% w/w.

Various useful binders include, but are not limited to acacia, guar gum, alginic acid, sodium alginate, dextrin, carbomer, maltodextrin, methylcellulose, ethyl cellulose, hydroxyethyl cellulose, hydroxypropyl cellulose (HPC) (e.g., KLUCEL®), hydroxypropyl methylcelulose (HPMC) (e.g., METHOCEL®), hydroxyethylmethyl cellulose, carboxymethyl cellulose sodium, cottonseed oil, povidone (various grades of KOLLIDON®, PLASDONE®), ceratonia, dextrose, polydextrose, starch, gelatin, pregelatinized starch, hydrogenated vegetable oil type I, maltodextrin, microcrystalline cellulose, polyethylene oxide, Polymethacrylates and mixtures thereof. Binder can be present in powder form or as a dispersion or mixture of both. Binder is present in an amount from about 0.1 to about 70% which is present either in intra-granular or in extra-granular part of the composition. Preferably, the amount of binder is from about 0.5% to about 15% w/w. More preferably, the amount of binder is less than 3% or more than 10% w/w. Binder can be present in intra-granular part of the composition in dry powder for and/or in dispersion form (as granulation liquid). More preferably, Binder is present in intra-granular part of the composition in dispersion form (granulation liquid).

Various useful disintegrants and/or super-disintegrants include, but are not limited to croscarmellose sodium, carboxymethyl cellulose sodium, carboxymethyl cellulose calcium, povidone, crospovidone, polacrilin potassium, sodium starch glycolate, alginic acid, sodium alginate, calcium phosphate tribasic, colloidal silicon dioxide, docusate sodium, guar gum, low substituted hydroxypropyl cellulose (L-HPC), magnesium aluminum silicate, methylcellulose, microcrystalline cellulose, silicified microcrystalline cellulose, starch or pre-gelatinized starch and/or combinations thereof. Disintegrant and/or super-disintegrants is present in an amount from about 0.1 to about 70% which is present either in intra-granular or in extra-granular part of the composition. Preferably, the amount of disintegrant is from about 0.5% to about 15% w/w.

Pharmaceutically acceptable lubricants include stearic acid, Zinc stearate, sucrose stearate, sodium benzoate, hydrogenated vegetable oil type I, calcium stearate, adipic acid, glyceryl palmitostearate, glycerine monostearate, medium-chain triglycerides, sodium stearyl Fumarate, glyceryl behenate, sodium lauryl sulphate, sodium stearyl fumarate, magnesium lauryl sulphate, magnesium stearate, polyethylene glycol. Preferably, lubricant is magnesium stearate. The amount of lubricant is from about 0.1% to about 10% w/w. More preferably, the amount of lubricant is form about 0.25% to about 2% w/w.

Surfactants or surface-active agents improve wettability of the dosage form and/or enhance its dissolution. Surfactants contemplated in the present invention include, but are not limited to, anionic surfactants, amphoteric surfactants, non-ionic surfactants and macromolecular surfactants. Surfactant may constitute from about 0% to about 5% by weight of composition.

Suitable glidants include, but are not limited to, calcium silicate, magnesium silicate, magnesium trisilicate, stearic acid and its derivatives or esters like magnesium stearate, calcium stearate and sodium stearate and the corresponding esters such as sodium stearyl fumarate; talc and colloidal silicon dioxide, tribasic calcium phosphate, starch or mixtures thereof. Preferably, the amount of glidant is from about 0 to about 10.0% w/w.

Other carrier materials (such as anti-adherents, solubilizer, stabilizer, colorants, flavors, sweeteners and preservatives) that are known in the pharmaceutical art may be included in composition of the present invention.

The high drug load solid oral tablet dosage form prepared by the above process can be subjected to in vitro dissolution evaluation according to Test 711 "Dissolution" in the United States Pharmacopoeia 37, United States Pharmacopoeial Convention, Inc., Rockville, Md., 2014 ("USP") to determine the rate at which the active substance is released from the dosage form, and the content of the active substance can be determined in solution by high performance liquid chromatography. When comparing the test and reference products, dissolution profiles should be compared using a similarity factor ($f_2$). The similarity factor is a logarithmic reciprocal square root transformation of the sum of squared error and is a measurement of the similarity in the percent (%) of dissolution between the two curves.

$$f_2 = 50 \cdot \log\{[1+(1/n)\Sigma_{t=1}^{n}(R_t-T_t)^2]^{-0.5} \cdot 100\}$$

Two dissolution profiles are considered similar when the $f_2$ value is equal to or greater than 50.

In another embodiment, high drug load solid oral pharmaceutical composition of the present invention exhibits more than 80% of drug release within 30 minutes in 1000 ml of of Acetate Buffer, pH 4.5 (Office of Generic Drugs dissolution database) using a USP II apparatus (paddle) at a temperature of 37±0.5° C. and a rotation speed of 100 revolutions per minute.

In another embodiment, solid oral pharmaceutical composition of the present invention particularly tablet dosage form of present invention may be packaged in HDPE bottles or blister packs. HDPE bottles may optionally contain desiccants.

As used herein, the term "about" means±approximately 20% of the indicated value, such that "about 10 percent" indicates approximately 08 to 12 percent.

Having described the invention with reference to certain preferred embodiments, other embodiments will become apparent to one skilled in the art from consideration of the specification. The invention is further defined by reference to the following examples describing in detail method for the preparation and testing of Eslicarbazepine acetate pharmaceutical composition. It will be apparent to those skilled in the art that many modifications, both to materials and methods, may be practiced without departing from the scope of the invention. Following examples are set out to illustrate the invention and do not limit the scope of the present invention.

Example 1

Eslicarbazepine acetate tablets were prepared by using quantitative formula as given in Table 1:

TABLE 1

| Sr. No. | Ingredient | Function | Quantity/Tablet (% w/w) |
|---|---|---|---|
| | Intra-Granular | | |
| 1. | Eslicarbazepine acetate | Active Ingredient | 30-95 |
| 2. | Lactose or Microcrystalline Cellulose | Diluent | 0-20 |
| 3. | HPMC or HPC | Binder | 0-15 |
| 4. | Sodium Starch Glycolate or L-HPC or Crospovidone | Disintegrant | 0-12 |
| 5. | Sodium lauryl sulfate | Surfactant | 0-2 |
| | Extra-Granular | | |
| 6. | Magnesium stearate | Lubricant | 0.1-5 |

Preparation Method:
i) Eslicarbazepine acetate, disintegrant, binder and optionally diluent and surfactant were sifted through ASTM #20 sieve.
ii) The sifted blend of step i) was mixed in a suitable blender for 5 minutes and compacted using a roller compactor.
iii) The compacts from step ii) were milled using ASTM #25 sieve.
iv) Blend from step iii) was lubricated with magnesium stearate.
v) The blend of step iv) was compressed into tablets using suitable punches.

Example 2

Eslicarbazepine acetate tablets were prepared by using quantitative formula as given in Table 2:

TABLE 2

| Sr. No. | Ingredient | Function | Quantity/Tablet (% w/w) |
|---|---|---|---|
| | Intra-Granular | | |
| 1. | Eslicarbazepine acetate | Active Ingredient | 80-95 |
| 2. | HPMC | Binder | 0-2.9 |
| 3. | Croscarmellose sodium | Disintegrant | 0-12 |
| 4. | Purified Water | Granulation Liquid | q.s. |
| | Extra-Granular | | |
| 5. | Magnesium stearate | Lubricant | 0.1-5 |

Preparation Method:
i) Eslicarbazepine acetate and disintegrant were sifted through ASTM #20 sieve.
ii) The sifted blend of step i) was mixed for 5-10 minutes.
iii) Binder was dissolved in purified water to prepare binder solution.
iv) Step ii) blend was granulated using binder solution of step iii).
v) The granules of step iv) were dried and optionally sifted and/or milled through ASTM #25 sieve.
vi) Lubricant was sifted through ASTM #60 sieve and added to step v) granules and mixed for 5-10 minutes.
vii) The blend of step vi) was compressed into tablets using suitable punches.

Example 3

Eslicarbazepine acetate tablets were prepared by using quantitative formula as given in Table 3:

TABLE 3

| Sr. No. | Ingredient | Function | Quantity/Tablet (% w/w) |
|---|---|---|---|
| | Intra-Granular | | |
| 1. | Eslicarbazepine acetate | Active Ingredient | 80-95 |
| 2. | Microcrystalline Cellulose | Diluent | 0-20 |
| 3. | HPMC or HPC (dry and/or dispersion) | Binder | 0-15 |
| 4. | Croscarmellose sodium or Sodium Starch Glycolate or L-HPC | Disintegrant | 0-12 |
| 5. | Purified Water | Granulation Liquid | q.s. |
| | Extra-Granular | | |
| 6. | Magnesium stearate | Lubricant | 0.1-5 |

Preparation Method:
i) Eslicarbazepine acetate, disintegrant and optionally diluent were sifted through ASTM #20 sieve.
ii) The sifted blend of step i) was mixed for 5-10 minutes.
iii) Binder was dissolved in purified water to prepare binder solution.
iv) Step ii) blend was granulated using binder solution of step iii)
v) The granules of step iv) were dried and optionally sifted and/or milled through ASTM #25 sieve.
vi) Lubricant was sifted through ASTM #60 sieve and added to step v) granules and mixed for 5-10 minutes.
vii) The blend of step vi) was compressed into tablets using suitable punches.

Example 4

Eslicarbazepine acetate tablets were prepared by using quantitative formula as given in Table 4:

TABLE 4

| Sr. No. | Ingredient | Function | Quantity/Tablet (% w/w) |
|---|---|---|---|
| | Intra-Granular | | |
| 1. | Eslicarbazepine acetate | Active Ingredient | 30-95 |
| 2. | Lactose | Diluent | 0-20 |
| 3. | HPMC or HPC | Binder | 0-2.9 |
| 4. | Purified Water | Granulation Liquid | q.s. |
| | Extra-Granular | | |
| 5. | Croscarmellose sodium or Sodium Starch Glycolate or L-HPC | Disintegrant | 0-12 |
| 6. | Magnesium stearate | Lubricant | 0.1-5 |

Preparation Method:
i) Eslicarbazepine acetate and optionally diluent were sifted through ASTM#20 sieve.
ii) The sifted blend of step i) was mixed for 5-10 minutes.
iii) Binder solution was prepared by dissolving/dispersing binder in granulation liquid.
iv) Step ii) blend was granulated using step iii) binder solution.
v) The granules of step iv) were dried and optionally sifted and/or milled through ASTM#25 sieve.
vi) Disintegrant and Lubricant were sifted through a suitable sieve and added to step v) granules and mixed for a 5-10 minutes.
vii) The blend of step vi) was compressed into tablets using suitable punches.

Example 5

Eslicarbazepine acetate tablets were prepared by using quantitative formula as given in Table 5:

TABLE 5

| Sr. No. | Ingredient | Function | Quantity/Tablet (% w/w) |
|---|---|---|---|
| | Intra-Granular | | |
| 1. | Eslicarbazepine acetate | Active Ingredient | 30-95 |
| 2. | HPMC | Binder | 0.1-15 |
| 3. | Sodium Starch Glycolate | Disintegrant | 0.1-12 |
| 4. | Purified Water | Granulation Liquid | q.s. |
| | Extra-Granular | | |
| 5. | Magnesium stearate | Lubricant | 0.1-5 |

Preparation Method:
i) Eslicarbazepine acetate and disintegrant were sifted through ASTM #20 sieve.
ii) The sifted blend of step i) was mixed for 5-10 minutes.
iii) Binder solution was prepared by dissolving binder in water.
iv) Step ii) blend was granulated using step iii) binder solution.
v) The granules of step iv) were dried and optionally sifted and/or milled through ASTM#25 sieve.
vi) Lubricant was sifted through ASTM #60 sieve and added to step v) granules and mixed for 5-10 minutes.
vii) The blend of step vi) was compressed into tablets using suitable punches.

Example 6

Eslicarbazepine acetate tablets were prepared by using quantitative formula as given in Table 6:

TABLE 6

| Sr. No. | Ingredient | Function | Quantity/Tablet (% w/w) |
|---|---|---|---|
| | Intra-Granular | | |
| 1. | Eslicarbazepine acetate | Active Ingredient | 90.1-95 |
| 2. | HPMC or HPC | Binder | 0-3 |
| 3. | Sodium Starch Glycolate or L-HPC or Crospovidone | Disintegrant/ Super-Disintegrant | 0.1-12 |
| 4. | Purified Water | Granulation Liquid | q.s. |
| | Extra-Granular | | |
| 5. | Magnesium stearate | Lubricant | 0.5-1.0 |

Preparation Method:
i) Eslicarbazepine acetate and disintegrant were sifted through ASTM #20 sieve.
ii) The sifted blend of step i) was mixed for 5-10 minutes.
iii) Binder solution was prepared by dissolving binder in granulation liquid.
iv) Step ii) blend was granulated using step iii) binder solution.
v) The granules of step iii) were dried and optionally sifted and/or milled through ASTM#25 sieve and optionally mixed the sifted granules.
vi) Lubricant was sifted through ASTM #60 sieve.
vii) Granules of step v) were lubricated with Lubricant.
viii) The blend of step vii) was compressed into tablets using suitable punches.

Example 7

The standardized method and equipment for testing dissolution time is provided in Office of Generic Drugs dissolution database. The dissolution profile of tablets dosage form prepared using quantitative composition as given in Example 2, 3 and 6 was measured in 1000 ml of Acetate Buffer, pH 4.5 (Office of Generic Drugs dissolution database) using a USP II apparatus (Paddle) at a temperature of 37±0.5° C. and a rotation speed of 100 revolutions per minute. The dissolution test was conducted on the reference formulation APTIOM® oral tablets in comparison to a tablet dosage form as given in Example 2, 3 and 6. The dissolution data is provided in Table 7.

TABLE 7

| Time point (min.) | % drug released | | | |
|---|---|---|---|---|
| | APTIOM ® | Example 2 | Example 3 | Example 6 |
| 5 | 35 | 39 | 42 | 54 |
| 10 | 63 | 56 | 68 | 69 |
| 15 | 77 | 69 | 76 | 77 |
| 20 | 82 | 80 | 80 | 78 |
| 30 | 87 | 87 | 85 | 84 |
| 45 | 90 | 90 | 88 | 88 |
| 60 | 92 | 92 | 91 | 90 |

Since, commercially available reference APTIOM® oral tablets and test formulations prepared using quantitative composition as given in Example 2, 3 and 6 exhibited more than 80% of drug release within 30 minutes, accordingly dissolution profiles of the all formulations were found to be similar to reference.

Results:

TABLE 8

| Elements | Results (Lab Scale) | Results (Industrial Scale) |
|---|---|---|
| Compressibility Index (%) | 21.4 | 20.7 |
| Hausner Ratio | 1.27 | 1.26 |
| Thickness (mm) | 6.05 | 6.14 |
| Friability (%) | 0.09 | 0.1 |
| Assay (%) | 99.2 | 98.2 |
| Dissolution (30 min) | 85 | 84 |

Example 8

Tablet dosage form prepared in Example 6 was subjected to Accelerated stability testing as per the ICH guidelines at temperature/relative humidity of 40°±2° C./75%±5% RH for 2 months. The tablet dosage form was placed in a high density polyethylene (HDPE) bottle with induction sealing and analyzed for drug content by High Performance Liquid Chromatography (HPLC) method. The prepared dosage form was found to be stable and exhibited following assay values (in Table 9):

TABLE 9

| Study Period | Acceptable limits | Amount of Eslicarbazepine acetate in the Tablet dosage form Example 6 |
|---|---|---|
| Initial | 90%-110% | 99.2% |
| After two months | 90%-110% | 99.4% |

Example 9

Two products are considered to be bioequivalent if the 90% confidence interval (CI) of the relative mean $C_{max}$, $AUC_{(0-t)}$ and $AUC_{(0-\infty)}$ of the test to reference should be within 80.00% to 125.00% in the fasting state. A bioequivalence study comparing the tablet dosage forms prepared in Example 6 (Test product, T) with commercially available Reference product APTIOM® Tablets (Reference product, R) was performed in eighteen healthy adult human subjects and plasma drug concentrations were determined at regular intervals after dosing. The following parameters were calculated for test and reference product:

$AUC_{0-t}$=Area under plasma drug concentration versus time curve, from time zero (drug administration) to the last measurable concentration.

$AUC_{0-inf}$=Area under the plasma drug concentration versus time curve, from time zero to infinity.

$T_{max}$=Time after dosing until the maximum measured plasma drug concentration.

$C_{max}$=Maximum plasma drug concentration.

T/R (Test vs Reference) ratio was determined for the calculated pharmacokinetic parameters and is tabulated in Table 10

TABLE 10

| Pharmacokinetic parameter | T/R Ratio (%) |
|---|---|
| $C_{max}$ | 105.31 |
| $AUC_{0-t}$ | 101.74 |
| $AUC_{0-inf}$ | 101.40 |

T/R ratio for AUC of about 101% indicates that the tablet dosage form prepared in Example 6 shows similar mean pharmacokinetic parameters when compared against commercially available reference product APTIOM® tablet which establishes that the tablet dosage form prepared in Example 6 was bioequivalent to the commercially available Reference product APTIOM® tablet.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention.

The invention claimed is:

1. A high drug load immediate release solid oral pharmaceutical composition in the form of a tablet having an intragranular portion and an extragranular portion, wherein:
the intragranular portion comprises eslicarbazepine acetate in an amount of 90.1% to 95% w/w of the composition, a binder being present in an amount of less than 3% w/w of the composition, and a disintegrant in an amount of between 0.1 and 12% w/w of the composition; and
the extragranular portion comprises a lubricant in an amount of between 0.5 and 1.0% w/w of the composition,
wherein the disintegrant and the binder are present in the intragranular portion of the composition and the extragranular portion of the composition is free of a disintegrant and a binder:
and the composition exhibits more than 80% of drug release within 30 minutes in 1000 ml of acetate buffer pH 4.5 using a USP II apparatus (Paddle) at a temperature of 37±0.5° C. and a rotation speed of 100 revolutions per minute.

2. The high drug load solid oral pharmaceutical composition according to claim 1, wherein the composition is free of any dry binder in the intragranular portion.

3. The high drug load solid oral pharmaceutical composition of claim 1, prepared by wet granulation process at industrial scale.

4. The high drug load immediate release solid oral pharmaceutical composition of claim 1, wherein the composition consists of the intragranular portion and the extragranular portion and the intragranular portion consists of eslicarbazepine acetate, a binder and a disintegrant; and the extragranular portion consists of a lubricant.

5. The high drug load immediate release solid oral pharmaceutical composition according to claim 4, wherein the disintegrant is selected from the group consisting of sodium starch glycolate, L-HPC, croscarmellose sodium and crospovidone.

6. The high drug load immediate release solid oral pharmaceutical composition according to claim 4, wherein the binder is selected from the group consisting of hydroxypropyl cellulose and hydroxypropyl methylcellulose.

7. The high drug load immediate release solid oral pharmaceutical composition according to claim 4, wherein the lubricant consists of magnesium stearate.

8. The high drug load immediate release solid oral pharmaceutical composition according to claim 7, wherein the magnesium stearate is present in an amount of between 0.5 and 1.0% w/w of the composition.

9. The high drug load immediate release solid oral pharmaceutical composition according to claim 4, wherein the intragranular portion is made by a wet granulation process.

10. A solid oral pharmaceutical composition in the form of a tablet having an intragranular portion and an extragranular portion, wherein:
the intragranular portion consists of eslicarbazepine acetate in an amount of 90.1% to 95% w/w of the composition, a binder being present in an amount of less than 3% w/w of the composition, and a disintegrant in an amount of between 0.1 and 12% w/w of the composition; and
the extragranular portion consists of a lubricant in an amount of between 0.5 and 1.0% w/w of the composition,
wherein the disintegrant and the binder are present in the intragranular portion of the composition and the extragranular portion of the composition is free of a disintegrant and a binder.

11. The solid oral pharmaceutical composition according to claim 10, wherein the composition is free of any dry binder in the intragranular portion.

12. The solid oral pharmaceutical composition of claim 10, wherein the tablet is prepared by a wet granulation process at industrial scale.

13. The solid oral pharmaceutical composition according to claim 10, wherein the disintegrant is selected from the group consisting of sodium starch glycolate, L-HPC, croscarmellose sodium and crospovidone.

14. The solid oral pharmaceutical composition according to claim 10, wherein the binder is selected from the group consisting of hydroxypropyl cellulose and hydroxypropyl methylcellulose.

15. The solid oral pharmaceutical composition according to claim 10, wherein the lubricant consists of magnesium stearate.

16. The solid oral pharmaceutical composition according to claim 15, wherein the magnesium stearate is present in an amount of between 0.5 and 1.0% w/w of the composition.

\* \* \* \* \*